US00PP22454P2

(12) United States Plant Patent
Blom

(10) Patent No.: US PP22,454 P2
(45) Date of Patent: Jan. 10, 2012

(54) ***CHRYSANTHEMUM* PLANT NAMED 'ZANMULISA'**

(50) Latin Name: ***Chrysanthemum×morifolium* Ramat.**
Varietal Denomination: Zanmulisa

(75) Inventor: Wilhelmus Bernardus Blom, Leimuiden (NL)

(73) Assignee: Chrysanthemum Breeders Association Research B.V., Valkenburg Z-H (NL)

( * ) Notice: Subject to any disclaimer, the term of this patent is extended or adjusted under 35 U.S.C. 154(b) by 0 days.

(21) Appl. No.: 12/923,739

(22) Filed: Oct. 6, 2010

(51) Int. Cl.
*A01H 5/00* (2006.01)

(52) U.S. Cl. ..... Plt./292

(58) Field of Classification Search ..... Plt./292
See application file for complete search history.

*Primary Examiner* — Annette Para
(74) *Attorney, Agent, or Firm* — Steptoe & Johnson LLP

(57) ABSTRACT

A *chrysanthemum* plant named 'Zanmulisa' characterized by its large sized daisy-type blooms with bright purple ray florets and prolific branching; and a response time of 7 weeks.

3 Drawing Sheets

Botanical designation: *Chrysanthemum×morifolium* Ramat.

Cultivar denomination: 'Zanmulisa'.

BACKGROUND OF THE INVENTION

The present invention relates to a new and distinct cultivar of *chrysanthemum* plant, botanically known as *Chrysanthemum×morifolium* Ramat., and hereinafter referred to by the cultivar denomination 'Zanmulisa'. 'Zanmulisa' is a product of a breeding and selection program for pot mums which had the objective of creating new cultivars with a daisy type inflorescence with medium plant height and a response week of 7 weeks. 'Zanmulisa' is a seedling resulting from a cross of the female parent id 44275 and the male parent id 20560. Plants of the new cultivar 'Zanmulisa' differ from plants of the female parent in inflorescence color; the female parents has red inflorescences, while the seedling has pink ones. Plants of the new cultivar 'Zanmulisa' differ from plants of the male parent in the following characteristics. (1) Inflorescence size. And (2) Response time. (1) The inflorescences of the male parent are smaller than those of the seedling. (2) The response time of the male parent is higher than that of the seedling.

The new and distinct cultivar was discovered and selected as a flowering plant within the progeny of the stated cross by Wilhelmus Bernardus Blom in a controlled environment (greenhouse) in Rijsenhout, The Netherlands in May 2006. The first act of asexual production of 'Zanmulisa' was accomplished when vegetative cuttings were taken from the initial selection in July 2006 and propagated further in a controlled environment in Rijsenhout, The Netherlands. The new cultivar has been found to retain its distinctive characteristics through successive propagations, although the phenotype may somewhat vary with variations in environment such as light intensity and temperature.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
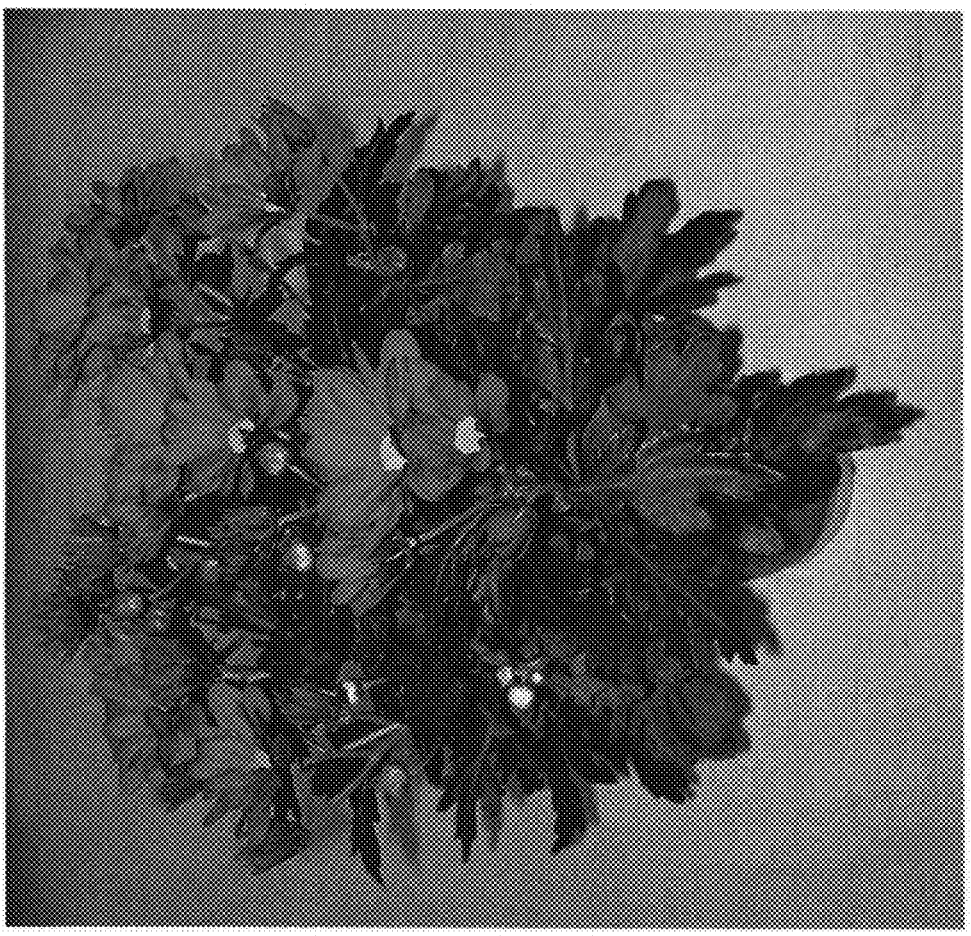
FIG. 1 shows a plant of the cultivar in full bloom.
Figure 2:
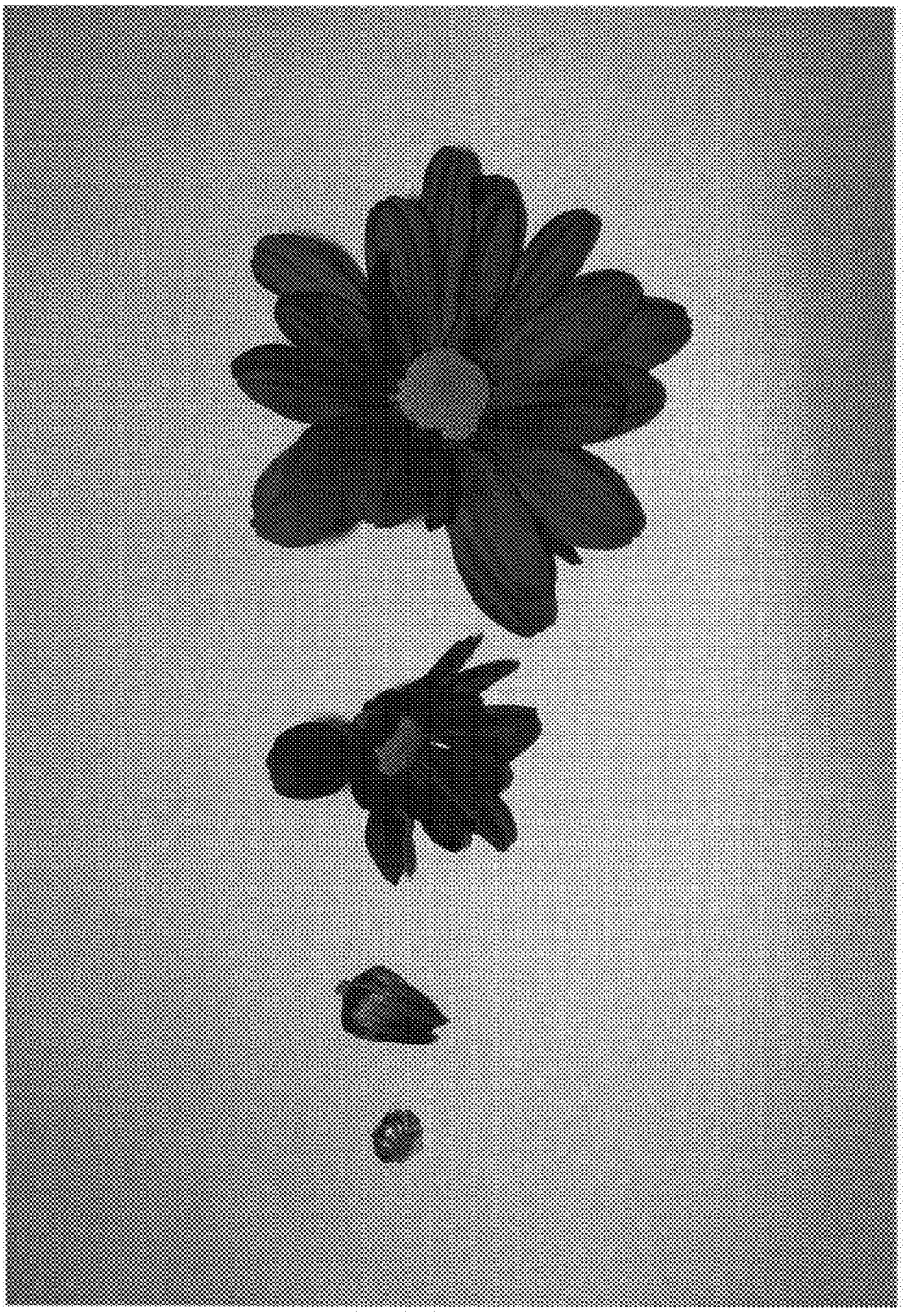
FIG. 2 shows the various stages of bloom of the new cultivar.
Figure 3:
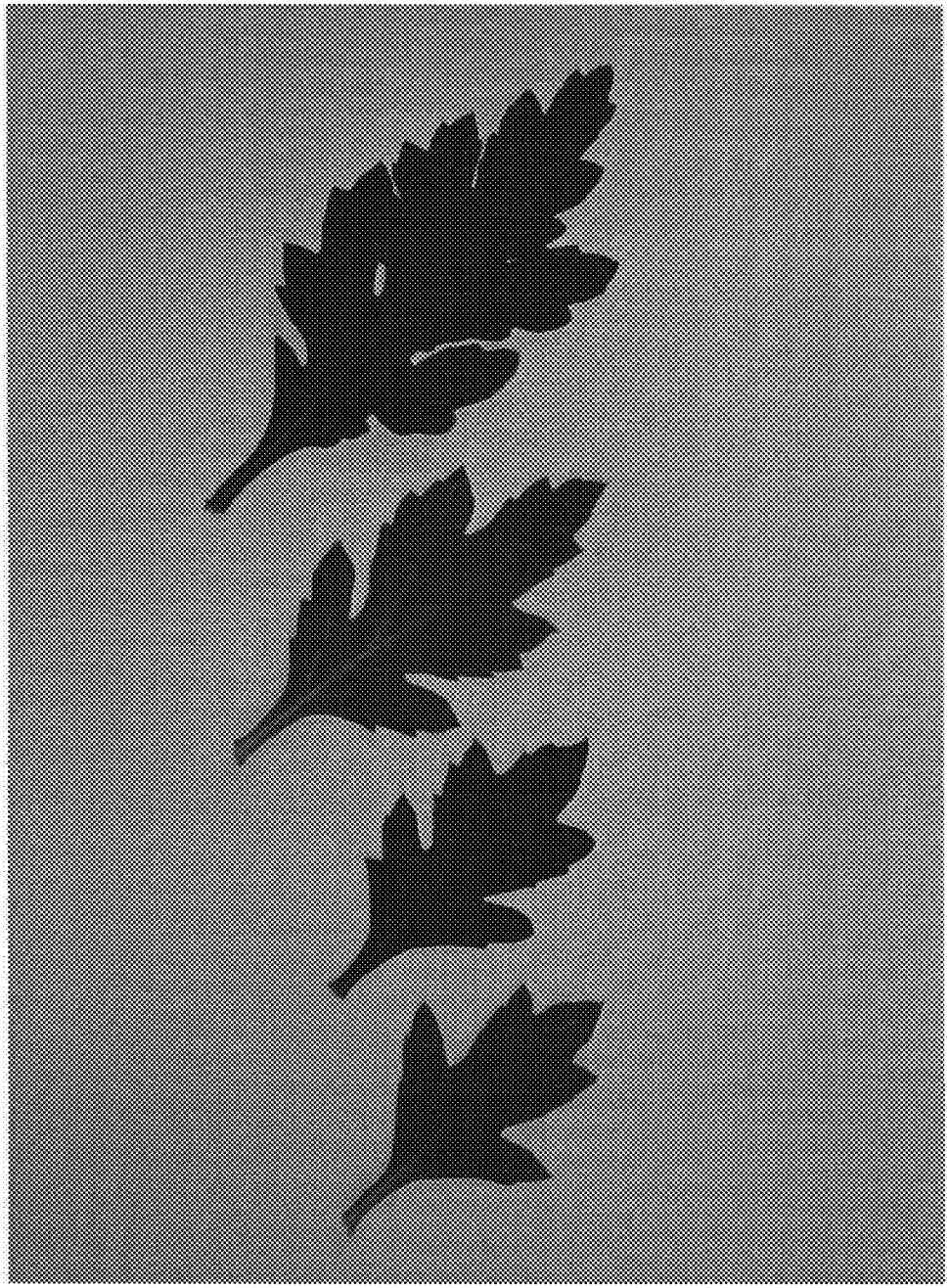
FIG. 3 shows the various stages of foliage of the new cultivar.

The observations and measurements were gathered in May 2010 from plants grown in a greenhouse in Rijsenhout, The Netherlands, in a photo-periodic controlled crop under conditions generally used in commercial practice. Three cuttings were planted in a pot with a diameter of 12 cm. The greenhouse temperatures for this crop were at day-time 18.degree.C. to 25.degree. C., and at night about 20.degree. C. The photo-periodic response time in this crop was 7 weeks after an average of eight long days. After this long day period growth retardants (Alar) were applied six times in an average dose of 1.5 gram/liter water until flowering. The plants were observed (directly) during the flowering of this crop. No tests were done on disease or insect resistance or susceptibility. No tests were done on cold or drought tolerance. To show the phenotype as described 'Zanmulisa' can be planted without assimilation lightning (high pressure sodium lamps) between week 50 and week 40 of the next year under greenhouse conditions in the Netherlands. With assimilation lightning (minimum level 2500 lux) it can be planted all year round under greenhouse conditions in the Netherlands.

This new variety produces large sized daisy-type blooms with purple ray florets and a response time of 7 weeks.

From the cultivars known to inventor the most similar existing cultivar in comparison to 'Zanmulisa' is 'Dark Pink Elgon' (U.S. Plant Pat. No. 12,492). When 'Dark Pink Elgon' and 'Zanmulisa' are being compared the following difference is noticed: The difference of 'Dark Pink Elgon' and 'Zanmulisa' are (1) Inflorescence size. And (2) Color ray-florets. (1) The inflorescences of 'Dark Pink Elgon' are smaller than those of 'Zanmulisa'. (2) The ray-florets of 'Dark Pink Elgon' are pink, while those of 'Zanmulisa' are more purple.

The following is a description of the plant and characteristics that distinguish 'Zanmulisa' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

| Botanical Description of *Chrysanthemum xmorifolium* Ramat. 'Zanmulisa' | |
|---|---|
| Bud | |
| Size | Medium; cross-section 6 mm, height 5 mm |
| Shape | Oblate |
| Texture | Pubescent |
| Outside Color | Greyed-green 191A |
| Phyllaries | |
| Number | 22, arranged in 3 rows |
| Shape | Elliptic |
| Apex | Acute |
| Base | Truncate |
| Margin | Entire |
| Color | Upper surface: Green N138B |
| Length and width | 1.2 cm; 2 mm |
| Texture | Pubescent |
| Inflorescence | |
| Type | Daisy |
| Height | 1.8 cm |
| Diameter | 7 cm |
| Peduncle length | 3.5 cm |
| Peduncle color | Green 137D |
| Peduncle diameter | 2 mm |
| Peduncle texture | Pubescent |
| Number per branch | Approx. 5 inflorescences |
| Shelf life | 4 weeks |
| Seeds | Produced in small quantities, ovate, Greyed-brown 199A, length 1.5 mm, diameter 0.6 mm |
| Fragrance | Faint *chrysanthemum* odor |
| Color | |
| Center of inflorescence (disc florets) | Immature stage: Yellow Green N144B<br>Mature stage: Yellow 7A |
| Color of upper surface of the ray-florets | Red-purple 71A |
| Color of the lower surface of the ray-florets | Red-purple 72C |
| Tonality from Distance | A pot *mum* with bright purple flowers and a green center |
| Color of the ray-florets after aging of the plant | Red-purple 71C |
| Ray florets | |
| Texture | Upper and lower side smooth |
| Number | 20-22 |
| Shape | Elliptic |
| Apex | Dentate |
| Base | Attenuate |
| Cross-section | Flat |
| Longitudinal axis of majority | Straight |
| Length of corolla tube | 0.4 cm |
| Ray-floret margin | Entire |
| Ray-floret length | 3-3.2 cm |
| Ray-floret width | 1-1.1 cm |
| Ratio length/width | Medium |
| Disc florets | |
| Disc diameter | 1.4 cm |
| Distribution of disc florets | Abundant |
| Shape | Tubular |
| Color | Yellow 11D at apex, Yellow-green 150D at base |
| Length | 4 mm |
| Diameter | 1 mm |
| Receptacle | |
| Color | Yellow-green 145D |
| Shape | Conical raised |

TABLE 1-continued

| Botanical Description of *Chrysanthemum xmorifolium* Ramat. 'Zanmulisa' | |
|---|---|
| Height | 5 mm |
| Diameter | 6 mm |
| Reproductive Organs | |
| Androecium | Present on disc florets only |
| Stamen length | 3 mm |
| Stamen color | Yellow-green 144A |
| Anther color | Yellow 3A |
| Pollen | Present |
| Pollen | Yellow 12A |
| Gynoecium | Present on both ray and disc florets |
| Style color | Yellow-green 154C |
| Style Length | 3 mm |
| Stigma color | Yellow 7A |
| Stigma Width | 1 mm |
| Ovary | Enclosed in calyx |
| Plant | |
| Form | Upright and branching |
| Growth habit | Spherical shape |
| Growth rate | Medium |
| Height | 24 cm |
| Width | 30 cm |
| Stem Color | Green 137C |
| Stem Strength | Strong |
| Stem Brittleness | Not brittle |
| Stem Anthocyanin Coloration | Not observed |
| Internode length | 1-1.5 cm |
| Length of lateral branch | From top to bottom 20 cm |
| Lateral branch color | Green 137D |
| Lateral branch diameter | 3 mm |
| Lateral branch, attachment | Medium strength |
| Branching (average number of lateral branches) | Prolific with 3 breaks after pinching |
| Response time | 7 weeks |
| Foliage | |
| Leaf color | Upper surface: Green 137A<br>Lower surface: Green 138A |
| Color midvein | Upper surface: Yellow-green 147D<br>Lower surface: Yellow-green 148D |
| Size | Medium; length 7-9.5 cm, width 3-4.5 cm |
| Quantity (number per lateral branch) | 12 |
| Shape | Elliptic |
| Texture upper side | Sparsely pubescent |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Acute |
| Apex | Mucronulate |
| Petiole length | 1 cm |
| Petiole diameter | 3 mm |
| Petiole color | Yellow-green 147D |

TABLE 2

| Differences with the comparison variety | | |
|---|---|---|
| | 'Zanmulisa' | 'Dark Pink Elgon' |
| Inflorescence size | 7 cm | 6 cm |
| Color ray-florets | Red-purple 71A | Red-purple 67B |

I claim:

1. A new and distinct *chrysanthemum* plant named 'Zanmulisa' as described and illustrated.

* * * * *